United States Patent [19]

Lotsof

[11] Patent Number: 5,591,738
[45] Date of Patent: Jan. 7, 1997

[54] METHOD OF TREATING CHEMICAL DEPENDENCY USING β-CARBOLINE ALKALOIDS, DERIVATIVES AND SALTS THEREOF

[75] Inventor: Howard S. Lotsof, Staten Island, N.Y.

[73] Assignee: NDA International, Inc., Staten Island, N.Y.

[21] Appl. No.: 322,490

[22] Filed: Oct. 14, 1994

[51] Int. Cl.$^6$ .......................... A61K 31/55; A61K 31/44
[52] U.S. Cl. .......................... 514/214; 514/292; 514/810; 514/811; 514/812; 514/813
[58] Field of Search .................................. 514/214, 292, 514/810, 811, 812, 813

[56] References Cited

PUBLICATIONS

Cappendijk, Susanne, et al; "The Inhibitory Effect of Norharman on Morphine Withdrawal Syndrome in Rats: Comparison with Ibogaine", *Behavioral Brain Research*, Faculty of Medicine and Health Sciences, Erasmus University Rotterdam, 3000 DR, Rotterdam, The Netherlands, Aug. 5, 1994, pp. 1–3.

Gunn, J. A., "Relations Between Chemical Constitution, Pharmacological ctions, and Therapeutic Uses, in the Harmine Group of Alkaloids", *The Pharmacological Laboratory, University of Oxford*, Mar. 14, 1935, pp. 379–383, 395–396.

Slotkin, Theodore A. and DiStefano, Victor; "A Model of Harmine Metabolism in the Rat", *The Journal of Pharmacology and Experimental Therapeutics*, Department of Pharmacology, University of Rochester, Rochester, New York, The Williams & Wilkins Co., vol. 174, No. 3, 1970, pp. 456–462.

Ho, Beng T. et al, "Metabolish of Harmaline in Rats", *Biochemical Pharmacology*, vol. 20, pp. 1313–1319, Pergamon Press, 1971, Great Britain.

Slotkin, Theodore A. et al, "Blood Levels and Urinary Exretion of Harmine and its Metabolites in Man and Rats", *The Jurnal of pharmacology and Experimental Therapeutics*, 1970, The William & Wilkins Co., vol. 173, No. 1, pp. 26–30, USA.

Slotkin, Theodore and DiStefano, Victor, "Urinary Metaboliytes of Harmine in the Rat and Theri Inhibition of Monoamine Oxidase" *Biochemical Pharmacology*, vol. 19, pp. 125–131, Pergamon Press, 1970, Great Britain.

Zetler, G. et al, "Pharmacokinetic in the Rat of the hallucinogenic Alkaloids Harmine and Harmaline", *Naunyn–Schmiedeberg's Arch. Pharmacol.* Springer–Verlag, 1974, pp. 285, 273–292.

Glick, S. D., et al, "Effects of *iboga* Alkaloids on Morphine and Cocaine Self-Administration in Rsats: Relationship to Tremorigenuc Effects and to Effects on Dopamine Release in Nucleus Accumbens and Striatum", *Brain Reseach*, Elsevier Science B. V., Jun. 7, 1994, pp. 14–22.

*Primary Examiner*—Kimberly Jordan
*Attorney, Agent, or Firm*—Oblon, Spivak, McClelland, Maier & Neustadt, P.C.

[57] ABSTRACT

A method of treating a chemical dependency disorder, an abuse syndrome or a combination thereof in a mammal in need thereof, which entails administering, to a mammal in need thereof, an amount of a β-carboline alkaloid, hydrolyzable derivative thereof or pharmaceutically-acceptable salt thereof effective to treat said chemical dependency disorder, abuse syndrome or a combination thereof in the mammal.

9 Claims, No Drawings

METHOD OF TREATING CHEMICAL DEPENDENCY USING β-CARBOLINE ALKALOIDS, DERIVATIVES AND SALTS THEREOF

BACKGROUND OF THE INVENTION

1. Field of the Invention

The present invention relates to a method of treating chemical dependency using β-carboline alkaloids, derivatives, and salts thereof.

2. Description of the Background

One class of plant indole alkaloids is the β-carboline alkaloids. There are presently 64 known β-carboline alkaloids dispersed throughout at least eight plant families. Schultes, R. E. et al., *The Botany and Chemistry of Hallucinogens*, C. C. Thomas, Springfield, Ill. All of the β-carboline alkaloids share a three ring nucleus designated 4-carboline by Perkin and Robinson. *Organic Chemistry: An Advanced Treatise*, Gilman (John Wiley and Sons, 1943). The first alkaloids of this class isolated were harmine and harmaline.

Harmine was first isolated from Peganum harmala seeds by Fritsche in 1847 (Bestandtheile der samen von Peganum harmala, Annalen 64:360–364), while harmaline was first isolated by Goegel in 1841 (*In German*, Isolation of Harmalol & Harmaline form Peganum harmala, Annalen 38:363 et seq.) A simplified extraction method using acetic acid was published by Hasenfratz in 1927 (*In German*, Extraction of Harmine and Harmaline from Peganum harmala, Ann. Chim. Phys. 10(7):151). Not until 1919, however, was the structure of harmaline established by Perkin and Robinson.

Thereafter, harmaline was first synthesized and its structure elucidated by Manske et al. (Manske RHF, Perkin, W. H., Robinson R, 1927, Part IX. Synthesis of harmaline, Jour. Chem. Soc. London, 1–15). Other syntheses of harmine and harmaline were accomplished by Akabori & Saito (1930, Synthesis of Harman and Harmine, Bericht 63:2245–2249); Spath and Lederer (1930, Synthese der Harmala alkaloids: Harmalin, Harmin, und Harman, Bericht 63:120–125); and Spencer (1959, A synthesis of Harmaline, Canadian Jour. Chem. 37:1851–1858).

One of the earliest reviews of the physiological activity of harmaline was that of Gunn, who proposed that harmaline be used to treat Malaria, (1909, Trans. Royal Soc. Edinburgh 47:245f). Similar assertions were subsequently made for harmine in 1911 (Trans. Royal Soc. Edinburgh 48:83f). In 1928, the efficacy of the harmala alkaloids to treat Parkinson's disease was noted, (1928, Uber ein neues auf das extrapyramidal-motorische system wirkendes alkaloid (Banisterine), Der Nervennarzt. 1:265–275).

Later, Chen et al established the LD 50 for harmine in mice and rabbits and further determined that sodium barbital limited toxicity (1939, Harmine, the Alkaloid of Caapi, Quart. Jour. Pharm. Pharmacol. 12:30–38). This paper additionally reviewed the pharmacology of known β-carboline alkaloids. Further contributions to the understanding of the harmala alkaloids were made by Gunn et 1935. Relations between Chemical Constitution, Pharmacological Actions, and Therapeutic Uses in the Harmine Group of Alkaloids; Arch. lnt'l. Pharmacodyn. Ther. 50:379–396).

More recently, it was demonstrated that harmaline is a monoamine oxidase inhibitor (Udenfriend S, Witcop B, Redfield B. G., Weissbach H, 1958, Studies with reversible inhibitors of monoamine oxidase: Harmaline and Related Compounds, Biochem. Pharmacol. 1:160–165). Lamarre et al. defined the cerebellar activity of harmaline in 1971 (Lamarre Y. et al, Harmaline-Induced Rhythmic Activity of Cerebellar and Lower Brain Stem Neurons, Brain Res. 32:246–250). In 1973, further studies of the physiological effects of harmaline were provided. (Harmaline-Induced Rhythmic Activity of Alpha and Gamma Motoneurons in the Cat, Brain Res. 63:430–434).

Even more recently, Singh et al ascertained neurotransmission and neurohormonal effects of harmaline. Further, harmaline, as a monoamine oxidase inhibitor, was shown to have an effect upon the concentration of dopamine and serotonin in the striatum of the cat with and without unilateral brainstem lesions, Canad. J. Physiol. Pharmacol. 45:897–904). However, the opposite effects of harmaline on serotonin and on dopamine and its metabolites, homovanillic acid and norepinephrine, in the brain of the cat, has also been noted, Canad. J. Physiol. Pharmacol. 46:585–589). Klein & Rowe studied the relationship of harmine, melatonin and serotonin (1970, Pineal gland in organ culture: Harmine Inhibition of Serotonin-C14 Oxidation is Accompanied by Stimulation of Melatonin-C14 Production, Mol. Pharmacol.6:164171). Given and Longenecker evaluated binding of harmine to human platelets (1983, Tetrahydroisoquinolines and β-carbolines: specific binding to human platelet alpha 2-receptors in vitro, Res. Commun. Chem. Pathol. Pharmacol. 41(2):349–352).

Clarification of the relationship of the harmala alkaloids and benzodiazepine receptors were presented by Robertson et al. (1981, Interactions of β-carbolines with the Benzodiazepine Receptor, Structure Activity Relationships, Eur. J. Pharmacol. 76:281) and by Rommelspacher et al. (1981, Benzodiazepine Antagonism by Harmine and Other β-carbolines In Vitro and In Vivo, Eur. J. Pharmacol. 70:409).

The effects of harmaline in psychotherapy were evaluated by Naranjo. (1969, Psychotherapeutic possibilities of new fantasy-enhancing drugs, Clin. Toxicol. 2(2):209–224). See also The Healing Journey (1975, 124–173, Harmaline and the collective unconscious, Pantheon Books, N.Y.).

Finally, a review of the field and the development of harmine from an historical and medical perspective is provided by Sanchez-Ramos. (1991, Banesterine and Parkinson's Disease, Clinical Neuropharmacology 14(5):391–401).

Thus, to date, harmine and harmaline have been used largely in physiological, particularly neurological, laboratory investigations. However, little attention has been given to clinical uses thereof.

At the same time, chemical dependencies continue unabated among all age groups, with neither young nor old persons being immune from chemical dependency disorders, abuse syndromes or combinations thereof. Presently, relatively "benign" drugs, such as methadone, are administered to persons as a substitute for drugs, such as heroin. However, this approach is only intended to minimize the adverse effects of drug withdrawal and does not reduce the underlying craving for the drug. Generally, efforts to date to combat drug abuse have focused on minimizing withdrawal symptoms. Little, or nothing, has been done to minimize craving for addictive substances.

Accordingly, it would be quite desirable if a compound or composition were known which, upon administration, afforded a reduced craving for a substance which causes chemical dependency disorders, abuse syndromes or a combination thereof in mammals.

SUMMARY OF THE INVENTION

Accordingly, it is an object of the present invention to provide a method for reducing craving for chemically-addicting substances in mammals.

Additionally, it is also an object of the present invention is to provide a method of treating chemical dependency disorders, abuse syndromes or combinations thereof in mammals.

It is, further, an object of the present invention to provide pharmaceutical compositions for treating chemical dependency disorders, abuse syndromes or conditions thereof in mammals.

The above objects and others are provided by a method of treating chemical dependency disorders, abuse syndromes or a combinations thereof in a mammal, which entails administering an effective amount of a β-carboline alkaloid, hydrolyzable derivative or pharmaceutically-acceptable salt thereof to a mammal in need thereof.

DETAILED DESCRIPTION OF THE PREFERRED EMBODIMENTS

In accordance with the present invention, it has been surprisingly discovered that the β-carboline alkaloids are effective in treating chemical dependency disorders, abuse syndromes or a combination thereof in mammals. The present invention affords a fresh approach to the treatment of such disorders and syndromes and provides a significant advantage over treatments based merely upon the alleviation of drug withdrawal symptoms. In essence, the present invention provides an effective method of treating chemical dependency disorders, abuse syndromes or combinations thereof by interrupting or attenuating the use of and craving for drugs which may cause abuse or dependence in mammals.

The present invention may be advantageously used in treating dependency and abuse in mammals which are dependent upon or which abuse any substance which tends to lead to addiction in mammals upon ingestion or administration. For example, heroin, fentanyl, methadone, morphine, codeine, phencyclidine, opium, alcohol, nicotine, cocaine, amphetamine, methamphetamine, caffeine or combinations thereof may be mentioned. Moreover, in accordance with the present invention, it makes no difference whether the chemically-addicting substances are ingested or administered in pure form or as found in nature in plant material, for example.

The present invention may also be advantageously used to treat chemical dependencies in mammals and chemical dependencies in mammals that may have been shown to be intractable to treatment by other agents.

In accordance with one aspect of the present invention, any single or combination of β-carboline alkaloids or hydrolyzable drivatives thereof or pharmaceutically acceptable salts thereof may be used as described herein.

Generally, any of the known 64 β-carboline alkaloids i.e. having the β-carboline ring nucleus may be used in accordance with the present invention.

For example, compounds such as harmine, harmaline, tetrahydroharmine, tetrahydronorharman, harmol, harmalol, ethyl harmol and n-butyl-harmol may be mentioned. However, any of the β-carboline alkaloids may be used. The chemical structures of these exemplary compounds are noted hereinbelow:

TABLE I

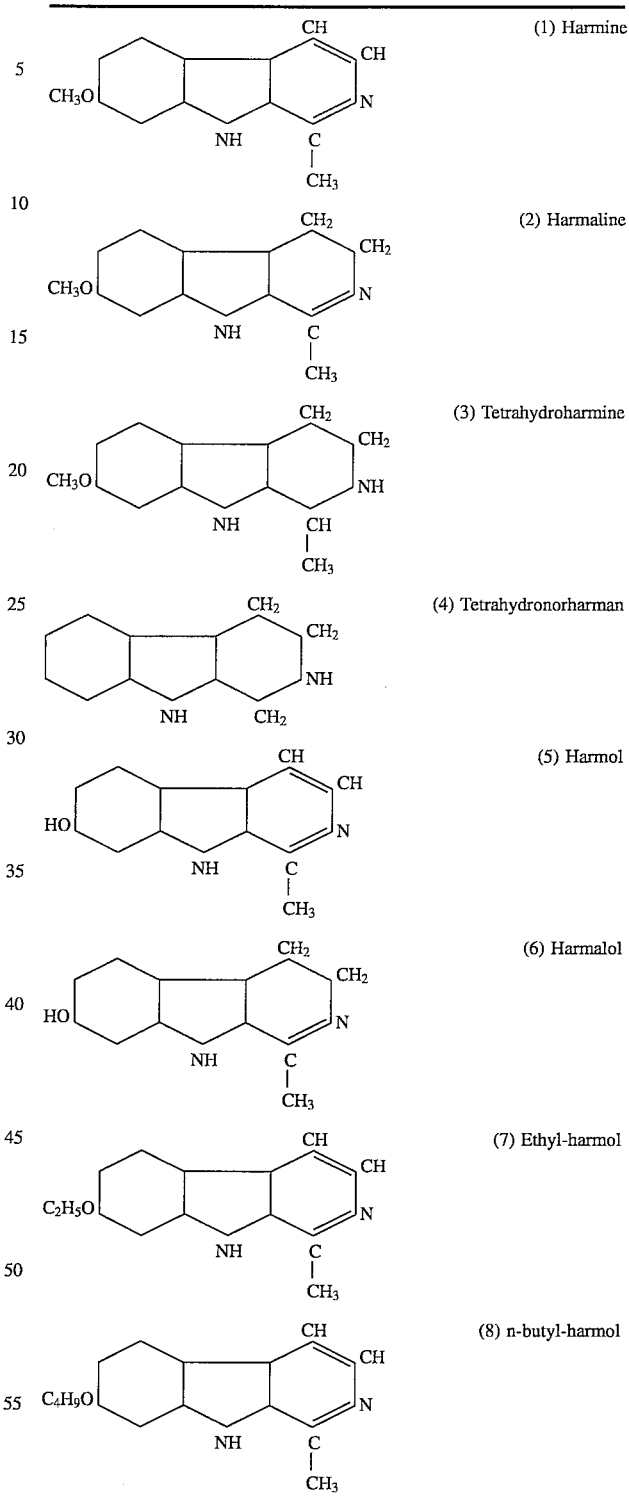

Additionally, any synthetic lower alkyl ether of harmol or harmalol may be used, wherein instead of HO— for harmol or harmalol, RO— is substituted therefor wherein R is 1 to 12 carbon atoms. For example, R may be $CH_3$—, $CH_3CH_2$—, $CH_3CH_2CH_2$—, $(CH_3)_2CH$—, $CH_3(CH_2)_2CH_2$— and $CH_3(CH_2)_3CH_2$—. Exemplary compounds are, for example, harmine, ethyl-harmol and n-butyl-harmol.

Moreover, in accordance with the present invention pharmaceutically-acceptable derivatives of the known β-carbolines may be used. As used herein, the term "derivative" means any compound which upon administration to a mammal, and with subsequent hydrolysis in vivo, will generate in vivo, one of the 64 β-carboline compounds described above. For example, the term "derivative" includes, but is not limited to, modified harmol and/or harmalol compounds, wherein the HO— of harmol and/or harmalol is esterified with carboxylic acids, acid anhydrides or acyl chlorides having 1 to 12 carbon atoms. It is preferred, however, that those compounds having 1 to 6 carbon atoms be used. For example, acids such as acetic acid and propionic acid, may be used, thereby forming the acetyl and propionyl group.

Furthermore, in addition to the free alkaloids, any pharmaceutically acceptable salt thereof may be used and conventionally prepared. Generally, any conventionally pharmaceutically-acceptable organic or inorganic acid addition salts may be used. For example, the hydrochloride, sulfate, phosphate, tannate, acetate or tartrate salts may be mentioned.

The present compounds, derivatives and/or salts thereof may be used alone or in combination with each other or as compositions in combination with pharmaceutically acceptable excipients. Additionally, any of the compounds, or salts mentioned above may be used in combination with ibogaine and compounds based thereupon as will be described below in more detail.

The compounds and/or compositions of the present invention are surprisingly effective in curbing mammalian affinity for substances having addictive potential. Furthermore, these compounds and compositions containing the same are effective over both the short and the long term.

Moreover, the administration of the present compounds or combinations containing the same may be administered in dosage regimens including single or multiple administrations over a period of hours, days, weeks, months or years as deemed appropriate by the treating physician, veterinarian or research scientist.

Generally, the present substances or mixtures thereof are administered in an amount of at least about 0.005 mg/kg of body weight as specified in the dose regimen. The precise amount administered will vary as needed. It is preferred, however, if an amount of about 0.01 mg/kg to about 100 mg/kg is used. These amounts will vary as needed, however, in the judgment of the treating physician, veterinarian or researcher. Generally, the total amounts may be are those as described in U.S. Pat. Nos. 4,587,243; 4,857,523; 4,499,076; 5,026,697 and 5,152,994.

In accordance with the present invention, the substances, compounds or compositions thereof may be administered in any manner, such as orally, intravenously, intramuscularly, interperitoneally, or rectally, for example.

The present invention also provides pharmaceutical compositions for interrupting drug dependency or abuse in mammals. These compositions generally contain one or more compounds, derivatives or salts of the present invention in combination with a pharmaceutically acceptable carrier or with ibogaine and/or compounds related thereto. In particular, in another advantageous aspect of the present invention, the β-carboline alkaloids, hydrolyzable derivatives and/or pharmaceutically-acceptable salts thereof may be combined with ibogaine or a noribogaine compound of the formula:

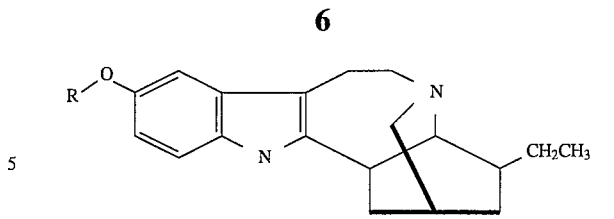

wherein R is hydrogen or a hydrolyzable group of the formula:

wherein X is an unsubstituted $C_1$–$C_{12}$ group or a $C_1$–$C_{12}$ group which is substituted by lower alkyl or lower alkoxy groups, wherein the noribogaine having the hydrolyzable group hydrolyzes in vivo to form 12-hydroxy ibogaine. Generally, the $C_1$–$C_{12}$ group is an alkyl group, either unsubstituted or substituted as described above.

However, it is preferred either that R be hydrogen or benzoyl, or that X be a $C_1$–$C_6$ alkyl group, which is unsubstituted or substituted by lower alkyl or alkoxy groups.

Generally, the lower alkyl or lower alkoxy groups have from 1 to about 6 carbon atoms.

Thus, the present invention also provides pharmaceutical compositions for treating chemical dependencies or abuse syndromes or both in mammals, which may contain any combination of β-carboline alkaloids, hydrolyzable derivatives thereof, ibogaine, 12-hydroxy ibogaine, hydrolyzable derivatives of 12-hydroxy ibogaine and pharmaceutically-acceptable salts of each and all of the above.

Any of these compositions may be used to treat a chemical dependency and/or abuse syndrome as broadly defined herein in any mammal suffering therefrom. As used herein the term "mammal" maybe a mouse, rat, rabbit,cat, dog, cow or chicken, for example, however, it is preferably a human.

Generally, any single compound, mixture of compounds or composition of the present invention may be administered such that the "active ingredients" are applied to the mammal in amounts and in manners described in any one of U.S. Pat. Nos. 4,587,243; 4,857,523; 4,499,076; 5,026,697 or 5,152, 994. However, administration regimens and precise amounts will depend upon the need of the patient mammal and the judgment of the attending physician, veterinarian or research scientist. Each of U.S. Pat. Nos. 4,587,243; 4,857,523; 4,499,076; 5,026,697 and 5,152,994 is incorporated herein in the entirety.

As used herein, the term "active ingredients" means any single compound or combination thereof from any of the following: β-carboline alkaloids, hydrolyzable derivatives thereof, ibogaine, 12-hydroxy ibogaine, hydrolyzable derivatives of 12-hydroxy ibogaine or pharmaceutically-acceptable salts of any of the above.

Further, the present substances or compositions may be compounded in any conventional manner using any conventional excipients. For example, the present compositions may be compounded as capsules, tablets, pills, powders, solutions or time-release formulations. Additionally, excipients such as conventional binders and/or fillers may be used.

Additionally, the present compounds and/or compositions containing the same may be formulated as a time-release composition using known formulations and methodologies.

For example, the present compounds and compositions may be microencapsulated in a lipid vesicle in accordance with a conventional encapsulation technique.

Additionally, the present compounds and/or compositions may be formulated using the methodologies of U.S. Pat.

Nos. 4,795,644; 5,112,621 and 5,275,824, all of which are incorporated herein by reference. That is, the present compounds and/or compositions may be pharmaceutically formulated using conventional excipients or fillers, such as starches, sugars or magnesium stearate, for example, and with standard coatings, such as gelatin, or may be formulated using time-release methodologies.

Further, the present compounds and/or compositions containing the same may be formulated into a cream, lotion or solution for topical administration, such as in U.S. Pat. Nos. 4,126,702 and 4,760,096. Additionally, the present compounds and/or compositions may be formulated as part of a skin-patch, as is presently used for Dramamine®, for example.

For purpose of definition, "chemical dependency disorders and/or substance abuse syndromes" consist of all pharmacological, physiological and psychological symptoms demonstrated by mammals using chemically-addictive substances, such as heroin, fentanyl, morphine, methadone, codeine, opium, cocaine salts, cocaine base, phencyclidine (PCP), alcohol, nicotine, caffeine or combinations thereof of these substances, for example, including natural and synthetic forms of thereof. Also, for purposes of the present invention, it makes no difference at all as to how these substances are ingested, i.e. whether smoked, injected, swallowed, snorted or by suppository.

Importantly, the chemical dependency or abuse treated in accordance with the present invention is not limited to heroin, morphine, methadone, codeine, opium, cocaine salts, cocaine base, alcohol, nicotine, or caffeine, including synthetic and natural forms of these substances. Rather, any type of chemical dependency or abuse may be treated thereby. As used herein, the terms "chemical dependency" and "abuse" are intended to mean dependency to or abuse by a mammal of any single chemical, mixtures of chemicals, natural or synthetic, which tend to promote repeated ingestion or administration thereof. Moreover, it is also specifically contemplated herein that the present invention be used to treat chemical dependencies and/or abuse syndromes arising from the use of any additive substance which is prospectively discovered or synthesized. As noted above, the mammals treated in accordance with the present invention may be humans, rats, mice, dogs, cats, rabbits or livestock, for example.

The compounds, hydrolyzable derivatives and/or salts of the present invention can be readily obtained by the artisan.

For example, the total synthesis of ibogaine has been reported. See Buchi, G. et al, *J. Am. Chem. Soc.*, 1966, 88, 3099 (1966); Rosenmund, P. et al, *Chem. Ber.*, 108, 1871 (1975) and Huffman et al, *J. Org. Chem.*, 50, 1460 (1985).

12-hydroxy ibogaine (noribogaine) may be synthesized by O-demethylation of ibogaine. This may be effected, for example, by reacting ibogaine with boron tribromide/methylene chloride at room temperature and isolating and purifying the product using known methodologies.

From noribogaine, any of the hydrolyzable esters thereof may be synthesized by reacting noribogaine with an appropriate carboxylic acid, anhydride or acyl chloride with or without a catalyst, such as pyridine, for example. For example, 12-hydroxy ibogaine can be reacted with acetic anhydride in the presence of pyridine, as a catalyst to yield 12-acetoxyibogainine. This specific example may be modified by using the appropriate acid, anhydride or acyl chloride to form any of these esters. The carboxylic acids, anhydrides and/or acyl chlorides so used are all either known compounds or can be readily prepared from known compounds using known reactions. Generally, esters of 1 to 12 carbon atoms are prepared, however, esters of 1 to 6 carbon atoms are more preferred.

The β-carboline alkaloids of the present invention are known compounds, as noted above. The hydrolyzable derivatives there of may be prepared by esterification of available hydroxyl groups, via esterification using conventional esterification reactions. For example, esterification with carboxylic acids, anhydrides or acyl chlorides with or without a catalyst, such as pyridine, may be used. More specifically, by way of example, compounds such as harmol and/or harmalol may be so esterified. The carboxylic acids, anhydrides and/or acyl chlorides so used are either known compounds or can be readily prepared from known compounds using conventional reactions. Generally, esters of 1 to 12 carbon atoms are prepared, however, esters of 1 to 6 carbon atoms are more preferred.

The pharmaceutically-acceptable salts of the present invention may be prepared using conventional acid-base reactions wherein the alkaloids and/or derivatives thereof constitute bases, an the inorganic and/or organic acids used constitute the acids. Conventional methods of recrystallization may be used to purify these salts.

In order to more fully describe the present invention, reference will now be made to certain examples which are provided solely for illustration and are not intended to be limitative.

EXAMPLE 1

Subjects were male Long Evans rats, weighing 175–200 grams at start. Rats were housed in individual cages in a temperature controlled room. They were kept on a 12:12 hour, light:dark cycle. Food and water were continuously available.

After four days of acclimatization to the animal room, rats were given a 2 percent solution of ethanol in a free choice paradigm with water. Water and ethanol were presented in Richter tubes mounted on the front of each cage. The next day, water only was given in the two tubes. The third day, the positions of the tubes were reversed and the concentration of ethanol was increased by 1 percent. This alternate day and alternate side exposure was repeated until a concentration of 10 percent ethanol was reached. The rats were then presented with a 10 percent ethanol solution for seven consecutive days. Tube position reversal was continued during this seven day period.

Harmaline HCl was dissolved in distilled water to a concentration of 8 mg/ml. Animals were divided into three groups receiving either saline, 20 mg/kg or 40 mg/kg of harmaline on alternate days.

Interperitoneal harmaline and saline administrations were carried out over a period of nine days on days one, three, five, seven and nine. The 40 mg/kg harmaline group consistently demonstrated a reduction of approximately two thirds that of the control group's ethanol consumption both during the treatment period and the ten day post treatment period.

EXAMPLE 2

A second experiment was conducted using a 10 mg/kg dose of harmaline administered interperitoneally on a daily basis for five days. Similar results were observed. The treated group showed ethanol consumption ranging from one half to one quarter that of control group during the five days of daily harmaline administration. The five day post treatment period showed the harmaline group drinking fifty to twenty five percent less ethanol than the control group.

Additional research showed harmine to produce similar physiological effects as harmaline at approximately 400 percent the dose of harmaline.

EXAMPLE 3

A twenty-three year old, 140 pound male human subject using one to three grams of cocaine daily via nasal administration was provided a single dose of 500 mg of harmaline HCl per os. Subject immediately discontinued cocaine use. Subject's cocaine use was interrupted for a period of four months. Subject had been previously treated with 500 mg of a total alkaloid extract of T. iboga with no significant effect on drug use. Conversely, it should be noted, however, that three persons successfully treated with ibogaine had no response to the administration of harmaline in interrupting their drug use.

EXAMPLE 4

A thirty-two year old, 136 pound male human subject using twenty dollars worth of heroin a day (approximately 40 mg/day) via IV route. The subject interspersed his use of heroin with 15 mg and 30 mg injections of morphine and unknown quantities of pantopon. The subject was given an IV injection of 100 mg of harmaline HCl. A second 100 mg IV injection of harmaline HCl was given six hours later. Subject discontinued heroin use for a period of three weeks after which contact with the subject was lost. Subject's cigarette consumption which had been between one and two packs a day immediately ceased. This continued for ten days after which subject began smoking at a reduced rate. It should be noted that IV administrations of harmala alkaloids are significantly more toxic than oral administrations and it is advised that they not be used in medical practice.

EXAMPLE 5

Male subject, twenty-four years of age, weighing 153 pounds was using 20 mg of heroin and 250 mg of cocaine per day both via IV route and was drinking twelve to sixteen cups of coffee per day. Subject was administered 750 mg of harmaline base in a split dose of 500 mg followed by 250 mg twenty minutes later. Subject's use of heroin and cocaine ceased immediately. Coffee consumption initially dropped to one half to one cup per day but, was increased to three to four cups per day within two weeks. Cocaine use ceased for a period of two months at which time subject began nasal use of approximately 50 mg/day. Within three months subject was using cocaine and amphetamine IV and barbiturates per os. Subject had not returned to heroin use at this time but, contact with the subject was lost and no further information was available.

EXAMPLE 6

Male subject, age twenty-two, estimated weight 120 pounds, using two grams of amphetamine and/or desoxyephedrine per day via IV route was administered 500 mg of harmaline base. Subject immediately ceased stimulant use. Contact was lost two weeks later when subject left city in which treatment was administered for location unknown.

The present invention, thus, affords an effective means of treating a chemical dependency disorder, an abuse syndrome or a combination thereof. The effectiveness thereof is evidenced by either a reduced or interrupted intake of substances tending to cause the disorder or syndrome. Thus, as described hereinabove, the treatment of the present invention leads to either a reduced or interrupted intake of such substances by the subject mammal. Further, this result may be obtained without generating a subsequent chemical dependency disorder or abuse syndrome based upon the treatment.

Having described the present invention, it will be apparent to one of ordinary skill in the art that many changes and modifications may be made to the embodiments described above without departing from the spirit and scope of the present invention.

What is claimed as new and is desired to be secured by Letters Patent of the United States is:

1. A pharmaceutical composition for treating a chemical dependency disorder, an abuse syndrome or a combination thereof in a mammal, which comprises as an active ingredient an effective amount of:

a) a first compound, comprising a β-carboline alkaloid, hydrolyzable derivative thereof or a pharmaceutically acceptable salt thereof or mixture thereof; and b) a second compound selected from the group consisting of a noribogaine compound of the formula:

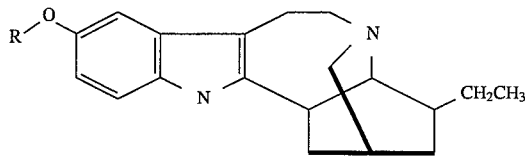

wherein R is hydrogen or a group of the formula

wherein X is an unsubstituted $C_1$–$C_{12}$ group or a $C_1$–$C_{12}$ group which is substituted by lower alkyl or lower alkoxy groups, and a pharmaceutically acceptable salt thereof.

2. The pharmaceutical composition of claim 1, wherein said β-carboline alkaloid of said first compound is selected from the group consisting of harmaline, harmine, tetrahydroharmine, tetrahydronorharman, harmol, harmalol, ethyl harmol, n-propyl harmol, isopropyl harmol and n-butyl harmol.

3. The pharmaceutical composition of claim 1, wherein said hydrolyzable derivative of said β-carboline of said first compound is selected from the group consisting of hydrolyzable esters of harmol and harmalol, said ester having 1 to 12 carbon atoms in an ester group thereof.

4. The pharmaceutical composition of claim 3, wherein said ester group has 1 to 6 carbon atoms therein.

5. The pharmaceutical composition of claim 1, wherein in said second compound, for said noribogaine compound, X is a $C_1$–$C_6$ group.

6. The pharmaceutical composition of claim 1, wherein in said second compound, for said noribogaine compound, R is hydrogen or benzoyl.

7. The pharmaceutical composition of claim 1, wherein the pharmaceutically-acceptable salt of the first compound is selected from the group consisting of hydrochloride, sulfate, phosphate, tannate, acetate and tartrate.

8. The pharmaceutical composition of claim 1, wherein the pharmaceutically-acceptable salt of the second compound is selected from the group consisting of hydrochloride, sulfate, phosphate, tannate, acetate and tartrate.

9. The pharmaceutical composition of claim 1, which further comprises a pharmaceutically-acceptable carrier.

\* \* \* \* \*